United States Patent [19]
Benson et al.

[11] Patent Number: 5,773,297
[45] Date of Patent: Jun. 30, 1998

[54] WATER ANALYSIS SYSTEMS

[75] Inventors: Richard Lynn Benson, St. Kilda; Ian Donald McKelvie, Nunawading; Alan David Stuart; Ian Campton Hamilton, both of New Lambton Heights, all of Australia

[73] Assignee: ADI Limited, Bondi Junction, Australia

[21] Appl. No.: 624,530

[22] PCT Filed: Oct. 11, 1994

[86] PCT No.: PCT/AU94/00616

§ 371 Date: Jul. 30, 1996

§ 102(e) Date: Jul. 30, 1996

[87] PCT Pub. No.: WO95/10780

PCT Pub. Date: Apr. 20, 1995

[30] Foreign Application Priority Data

Oct. 11, 1993 [AU] Australia ................ PM1740

[51] Int. Cl.⁶ .................................................. G01N 35/08
[52] U.S. Cl. ........................ 430/52; 422/78; 422/81; 436/103; 436/104
[58] Field of Search .................... 422/78, 81, 68.1; 436/52, 164, 175, 103–105

[56] References Cited

U.S. PATENT DOCUMENTS 3,699,004 10/1972 Skeggs .
3,703,355 11/1972 Takahashi et al. .
3,879,127 4/1975 Storr et al. .
4,013,413 3/1977 Stewart et al. .
5,215,715 6/1993 Haswell et al. ................ 422/81
5,420,039 5/1995 Renoe et al. ................... 436/52

FOREIGN PATENT DOCUMENTS

B-17542/88 12/1988 Australia .
0 486 156 A2 5/1992 European Pat. Off. .
1321079 6/1973 United Kingdom .

OTHER PUBLICATIONS

Derwent Abstract Accession No. 92–370635/45, Class S03, JP, A, 04–273066 (Yamada A) 29 Sep. 1992.

Primary Examiner—Jan Ludlow
Attorney, Agent, or Firm—Merchant, Gould, Smith, Edell, Welter & Schmidt, P.A.

[57] ABSTRACT

A method and apparatus for analysing a chemical species in a fluid are disclosed. The apparatus includes filtering apparatus (15, 17) upstream and downstream of the sample preparation section (3). The fluid is diverted from a line (1) by an arrangement of pumps (27) and valves through the upstream filter (15) to the digester (11) and through the downstream filter (17) out to the analyser/detector system (5). The pumps (27) and valve arrangement allows the purging of the sample preparation section (3) and backflushing of the filters (15, 17), the inlet line (7) and the outlet line (13).

9 Claims, 11 Drawing Sheets

WATER ANALYSIS SYSTEMS

The present invention relates to a method and an apparatus for analysing the concentration of a chemical species in a fluid.

The term "fluid" is understood herein to include, but is not limited to, heterogeneous liquid systems.

In particular, the present invention relates to a method and an apparatus for analysing the concentration of nutrients, such as phosphorus, in effluent streams from industrial plants and in rivers, lakes, reservoirs, estuaries, and other water systems that receive effluent streams from industrial plants and/or run-off which contains nutrients from agricultural and domestic sources.

The long-term discharge of phosphorus, typically in the form of phosphates, from industrial plants or agricultural pastoral land into water systems, such as rivers, lakes, reservoirs, and estuaries, leads invariably to algal growth which can cause significant problems. By way of example, some algal species are toxic to animals and humans and therefore represent an immediate and serious health problem. In addition, algal species which are nontoxic, whilst not presenting an immediate health problem, nevertheless have a significant adverse impact on the appearance, smell, and taste of water and therefore reduce water quality in water systems. Furthermore, in general terms, it is difficult and expensive to remove algal growth from water systems.

The accurate analysis of the concentration of phosphorus in water systems, particularly on a real time basis, is, an important factor in predicting and avoiding the growth of algal species.

One known procedure for analysing the concentration of phosphorus in water systems comprises periodic collection of samples, transportation of the samples to a laboratory, and analysis of the samples. In many instances, the procedure is unsatisfactory because of the expense involved in collection, transportation, and off-site analysis. In addition, the delay between collection and analysis may affect the accuracy of the analysis in view of the instability of the sample. Furthermore, the procedure is not carried out on a real-time basis and the delay between collection and analysis may make it difficult to adjust quickly the operating parameters of an industrial plant or otherwise take steps to prevent the release of excessive amounts of phosphorus into water systems.

Other known procedures for analysing the concentration of phosphorus in water systems, which are carried out on a real-time basis, are of limited value because the procedures measure soluble phosphorus only and not total phosphorus. The concentration of total phosphorus is considered to be a more important indicator of phosphorus bioavailability than the concentration of soluble phosphorus. Another problem with the known procedures is that the phosphorus level is distorted by build-up of biological material deposits on the lines of the analysis equipment with the result that there is a significant unpredictable background error associated with the measured phosphorus concentration.

It is an object of the present invention to provide a method and an apparatus for analysing the concentration of total phosphorus in water systems which alleviates the disadvantages and limitations of the prior art described above.

According to the present invention there is provided a method of analysing a chemical species in a fluid with an analyser/detector system, the analyser/detector system comprising (i) a sample preparation section having a means for placing the chemical species in a sample of the fluid into an analysable form and (ii) an analyser/detector, the method comprising:

(a) purging the sample preparation section with the fluid;

(b) transferring a sample of the fluid into the sample preparation section and placing the chemical species in the sample into the analysable form; and (c) transferring the sample with the chemical species in the analysable form into the analyser/detector and analysing the chemical species in the analyser/detector.

It is preferred that the method comprises transferring the sample through filtering means located upstream and downstream of the means for placing the chemical species in the sample into the analysable form.

It is preferred that the method comprises purging the upstream filtering means after transferring the sample to the analyser/detector to dislodge any solids retained in the upstream filtering means and to remove any biological material in the sample preparation section.

It is preferred that the method comprises purging the sample preparation section after transferring the sample to the analyser/detector to discharge any fluid remaining in the sample preparation section.

It is preferred particularly that the method comprises purging the sample preparation section after transferring the sample to the analyser/detector to discharge any fluid remaining in the sample preparation section and the filtering means and to dislodge any solids retained in the filtering means.

It is preferred that the method comprises placing the chemical species in the sample into the analysable form by digesting the chemical species with a digestion reagent to make analyzable the chemical species in the sample.

It is preferred that the purging steps described above be carried out with the digestion reagent.

According to the present invention there is also provided an apparatus for analysing a chemical species in a fluid, comprising:

(a) a sample preparation section having a means for placing the chemical species in a sample of the fluid into an analysable form; and (b) an analyser/detector for analysing the sample.

It is preferred that the apparatus comprises filtering means upstream and downstream of the sample preparation section.

It is preferred that the apparatus comprises a means for purging the upstream filtering means after transferring the sample to the analyser/detector to dislodge any solids retained in the filtering means and to remove any biological material in the sample preparation section.

It is preferred that the apparatus further comprises a means for purging the sample preparation section and the filtering means after transferring the sample to the analyser/detector to discharge any remaining fluid in the sample preparation section and the filtering means and to dislodge any solids retained in the filtering means.

It is preferred particularly that the means for placing the chemical species in the sample into the analysable form comprises a digester for making soluble the chemical species in the sample.

BRIEF DESCRIPTION OF THE DRAWINGS

The present invention is described further by way of example with reference to the accompanying drawings in which.

Figure 1:
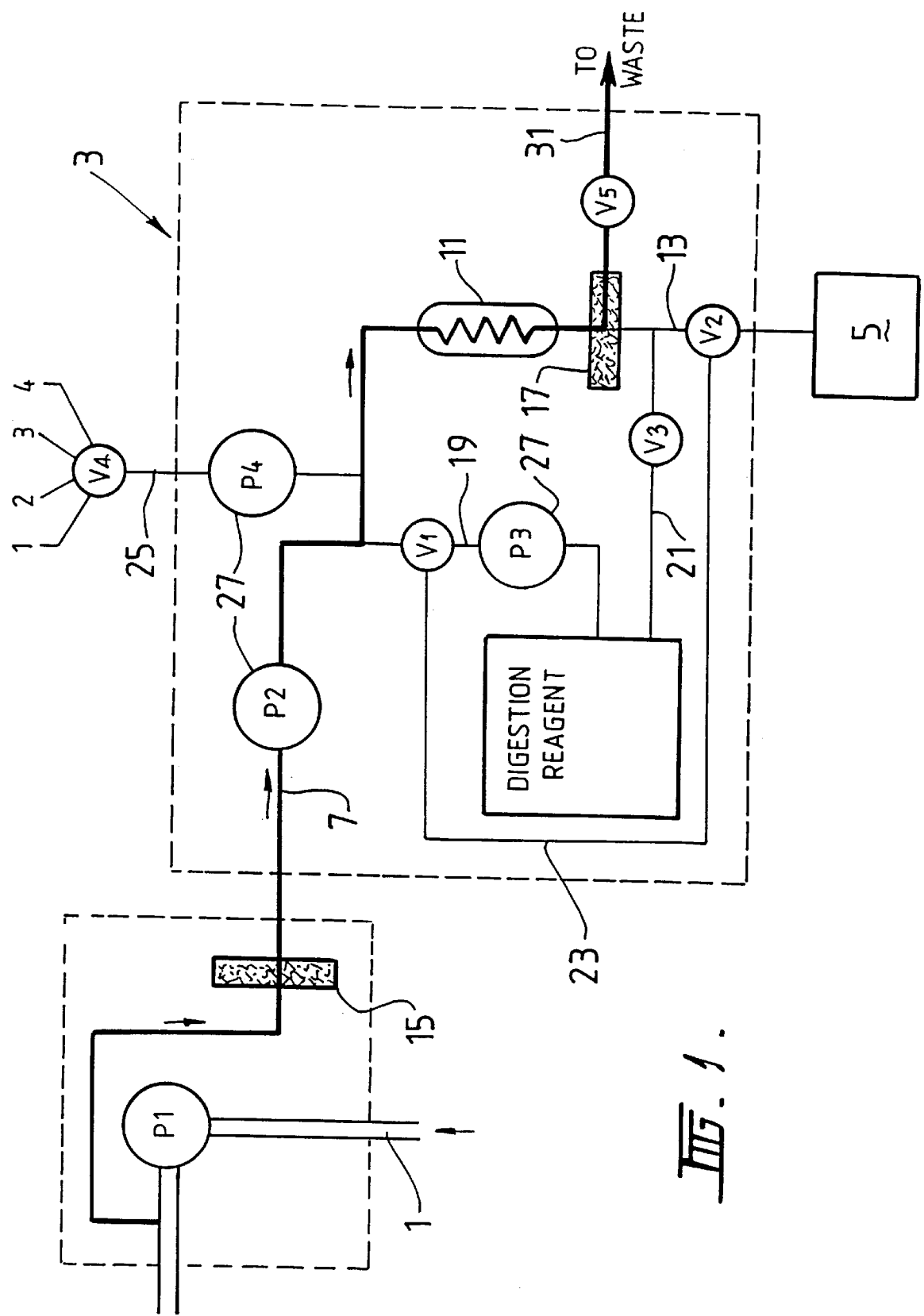
FIG. 1 is a schematic of the flow pattern of a first flushing step of the first embodiment of the invention.

The apparatus shown in FIGS. 1 to 5 is connected to an effluent line 1 from an industrial plant and is operable to analyse on a real-time basis the concentration of total phosphorus in the effluent. In this regard, the term "total" phosphorus is understood to mean the phosphorus in soluble and insoluble form in the effluent.

The apparatus comprises an analyser/detector system 5 for analysing the concentration of phosphorus in a sample of the effluent from the effluent line 1 and a sample preparation section generally identified by the numeral 3 for preparing the sample of the effluent for analysis in the analyser/detector system 5.

The analyser/detector system 5 is of any suitable type and configuration.

The sample preparation section 3 comprises an inlet line 7 connected to the effluent line 1, a digester 11 for digesting phosphorus in solid form, such as phosphates, in the effluent, a waste outlet line 31 for transferring the effluent to a waste sump (not shown), and an outlet line 13 for transferring the effluent from the digester 11 to the analyser/detector system 5.

The apparatus further comprises a 100 micron filter 15 in the inlet line 7 and a 0.45 micron filter 17 in the outlet line 13.

The apparatus further comprises:

(a) a reagent supply line 19 connected to the inlet line 7 upstream of the digester 11 for mixing a digestion reagent with the effluent in the inlet line 7 before the effluent reaches the digester 11; and (b) reagent supply lines 21, 23 connected to the outlet line 13 for supplying the digestion reagent selectively to purge the filter 17 (line 21) and to purge the sample preparation section 3 and the filter 15 (line 23).

The apparatus further comprises a standards supply line 25 connected to the inlet line 7 for supplying standards for calibrating the analyser/detector system 5.

The apparatus further comprises a series of peristaltic pumps 27 and valves V1, V2, V3, V4, and V5 in the inlet line 7, the reagent supply lines 19, 21, 23, the waste outlet line 31, the outlet line 13, and the standards supply line 25 which are selectively operable for pumping fluids through the apparatus as required to carry out one of the preferred embodiments of the method of the present invention, as described hereinafter.

The apparatus further comprises a microprocessor or other control means (not shown) to selectively operate the pumps 27 and valves V1, V2, V3, V4, and V5 in accordance with one of the preferred embodiments of the method of the invention, as described hereinafter.

With reference to FIG. 1, the first step in one of the preferred embodiments of the method of the present invention comprises purging the sample preparation section 3 and the filters 15, 17 with the effluent from the effluent line 1 to ensure that the sample of the effluent that is subsequently prepared in the sample preparation section 3 comprises the effluent only. In order to carry out the first step the valves V1, V2, V3, and V4 are closed, the valve V5 is opened, and the pump 27 in the inlet line 7 is operated to pump the effluent through the filter 15, the inlet line 7, the digester 11, and the filter 17, and thereafter through the waste outlet line 31 to the waste sump.

It is noted that in FIG. 1 and the other figures the flow of effluent is illustrated by thick lines and arrows.

Figure 2:
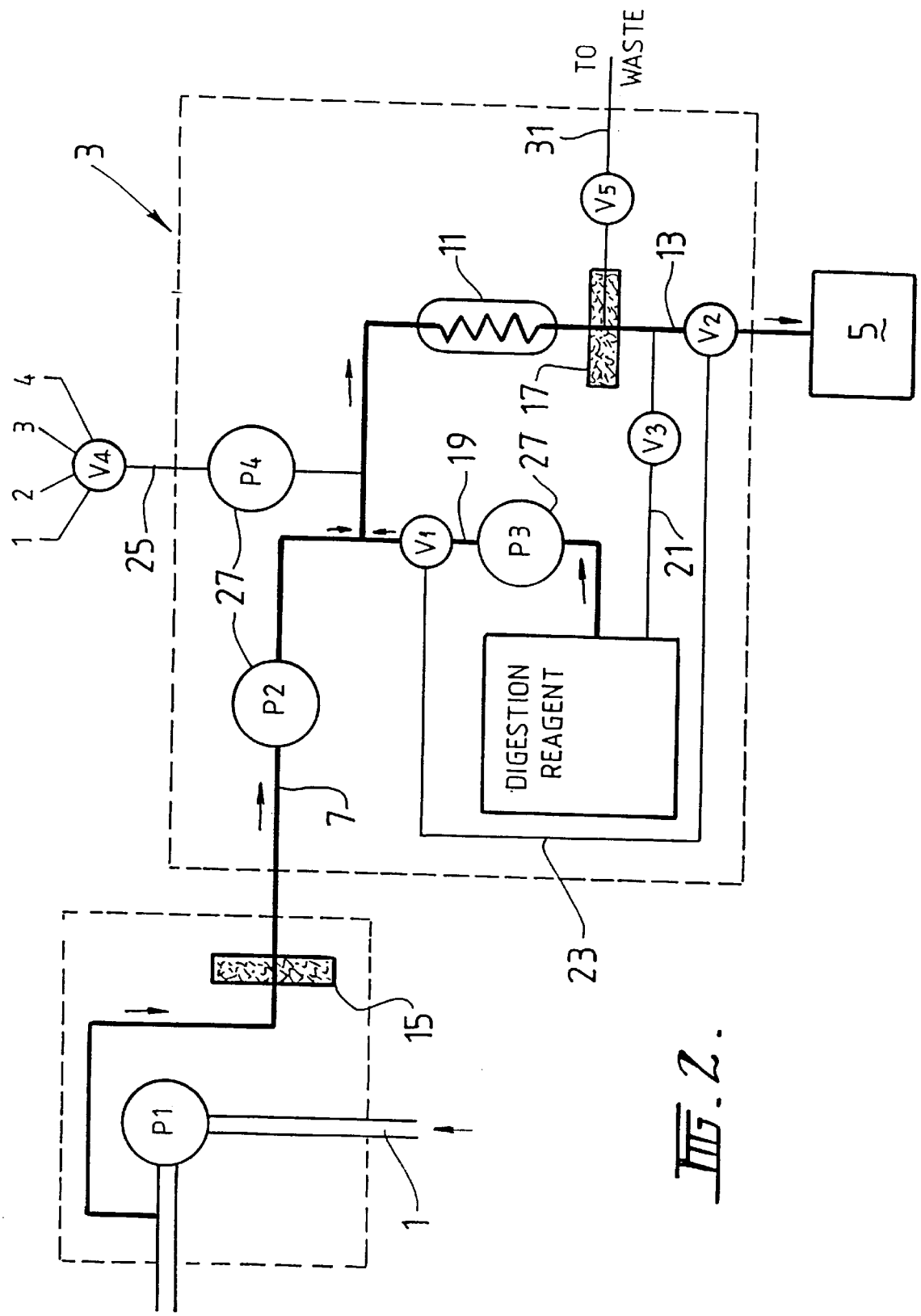
FIG. 2 is a schematic of the flow pattern of a second sample preparation step of the first embodiment of the invention.

With reference to FIG. 2, the second step of the method comprises preparing a sample of the effluent by mixing the digestion reagent with the effluent flowing through the inlet line 7 and digesting any solid forms of phosphorus in the effluent in the digester 11 and then transferring the sample to the analyser/detector system 5.

The digester 11 and the digestion reagent are of any suitable types and the operating parameters of the digester 11 are selected as required to ensure that all the solid forms of phosphorus in the effluent are placed into analysable form. The digester 11 may comprise one or more than one sub-system, allowing the sample of effluent to be heated, subjected to ultra-violet or microwave irradiation or such other conditions as may be necessary to place all the forms of phosphorus into solution.

It is preferred that the digester 11 operates at low temperature, in the order of 50°–150° C., preferably 80°–95° C. and at low pressure, in the order of 1–2 atmosphere.

It is also preferred that the digestion reagents and operating parameters be selected so that there is rapid digestion, typically within 3 to 10 minutes.

In order to carry out the second step, the valves V3, V4 and V5 are closed, the valves V1 and V2 are opened, and the pumps 27 in the inlet line 7 and the digestion reagent line 19 are operated to pump the effluent and the digestion reagent in the directions indicated by the arrows through the digester 11 and the analyser/detector system 5. The second step is carried out for a sufficient time for the analyser/detection system 5 to transfer a minimum volume of the effluent to the analyser/detector 5 to form an analysable sample.

Figure 3:
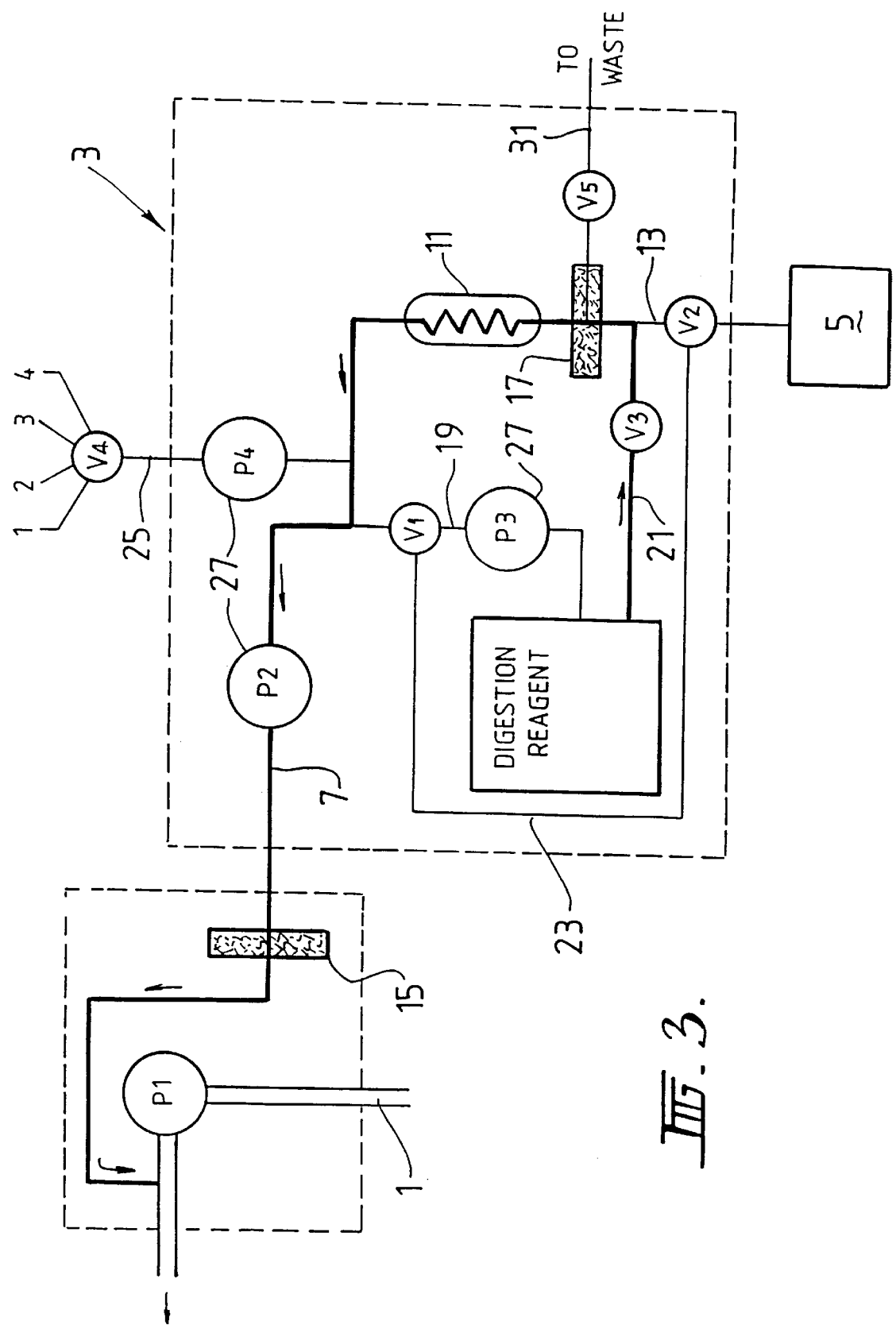
FIG. 3 is a schematic of the flow pattern of a third purging step of the first embodiment of the invention.

With reference to FIG. 3, the third step of the method comprises purging the sample preparation section 3 and the filters 15, 17 with digestion reagent to discharge any effluent therefrom and to dislodge and discharge any solids trapped in the filters 15, 17. In order to carry out the third step the valves V1, V2, V4 and V5 are closed, the valve V3 is opened, and the pump 27 in the inlet line 7 is operated to pump the digestion reagent in the direction indicated by the arrow, i.e. in a reverse direction to the previously described fluid flows, progressively through the filter 17, the digester 11, the inlet line 7, and the filter 15.

Figure 4:
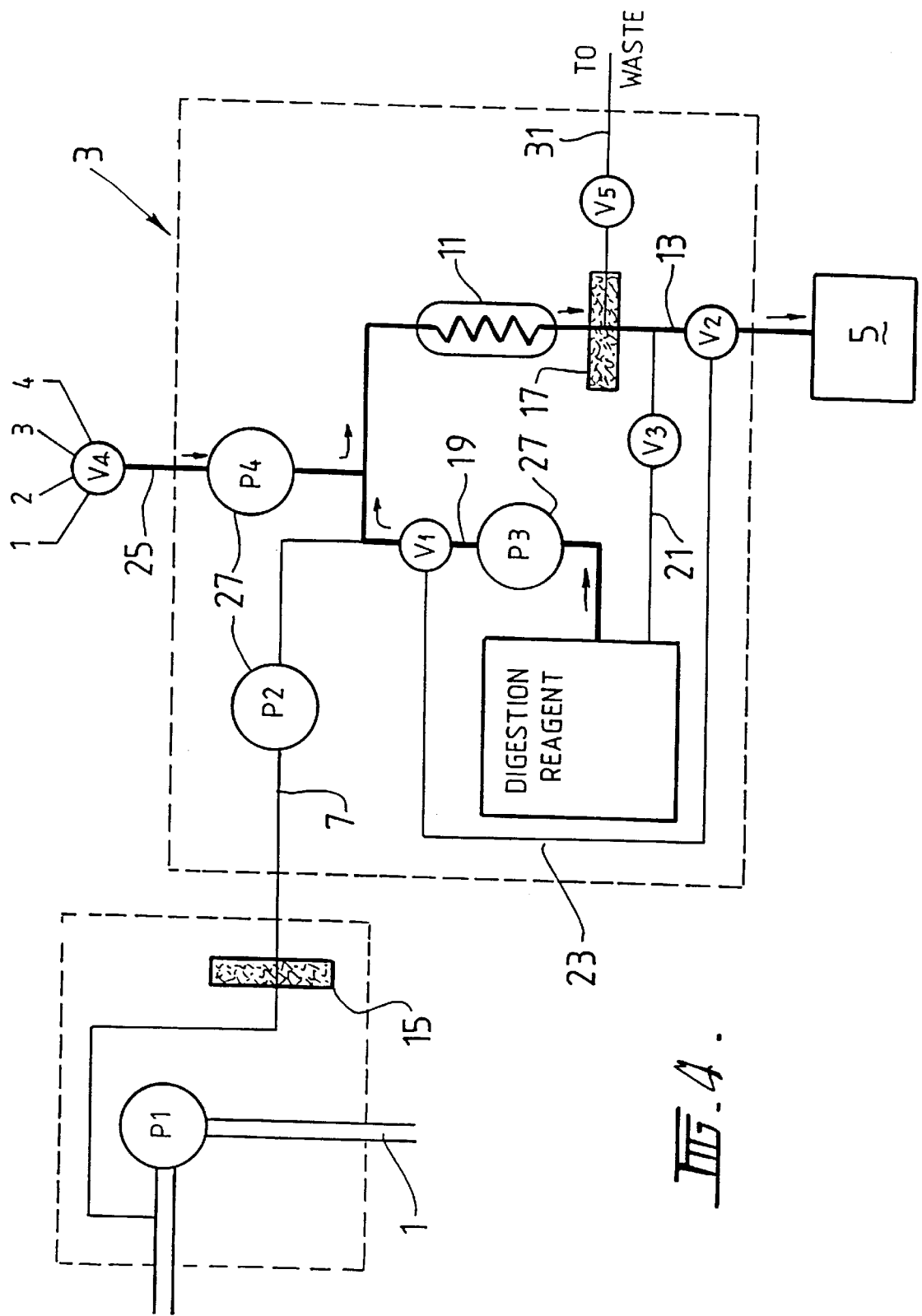
FIG. 4 is a schematic of the flow pattern of a fourth calibration step of the first embodiment of the invention.

With reference to FIG. 4, the fourth step of the method comprises calibrating the analyser/detector system 5. In order to carry out the fourth step the valves V3 and V5 are closed, the valves V1, V2, and V4 are opened, and the pumps 27 in the digestion reagent line 19 and the standards reagent line 25 are operated in the directions of the arrows to pump digestion reagent and standards reagent through the digester 11, the outlet line 13, and into the analyser/detector 5 to calibrate the analyser/detector 5.

Figure 5:
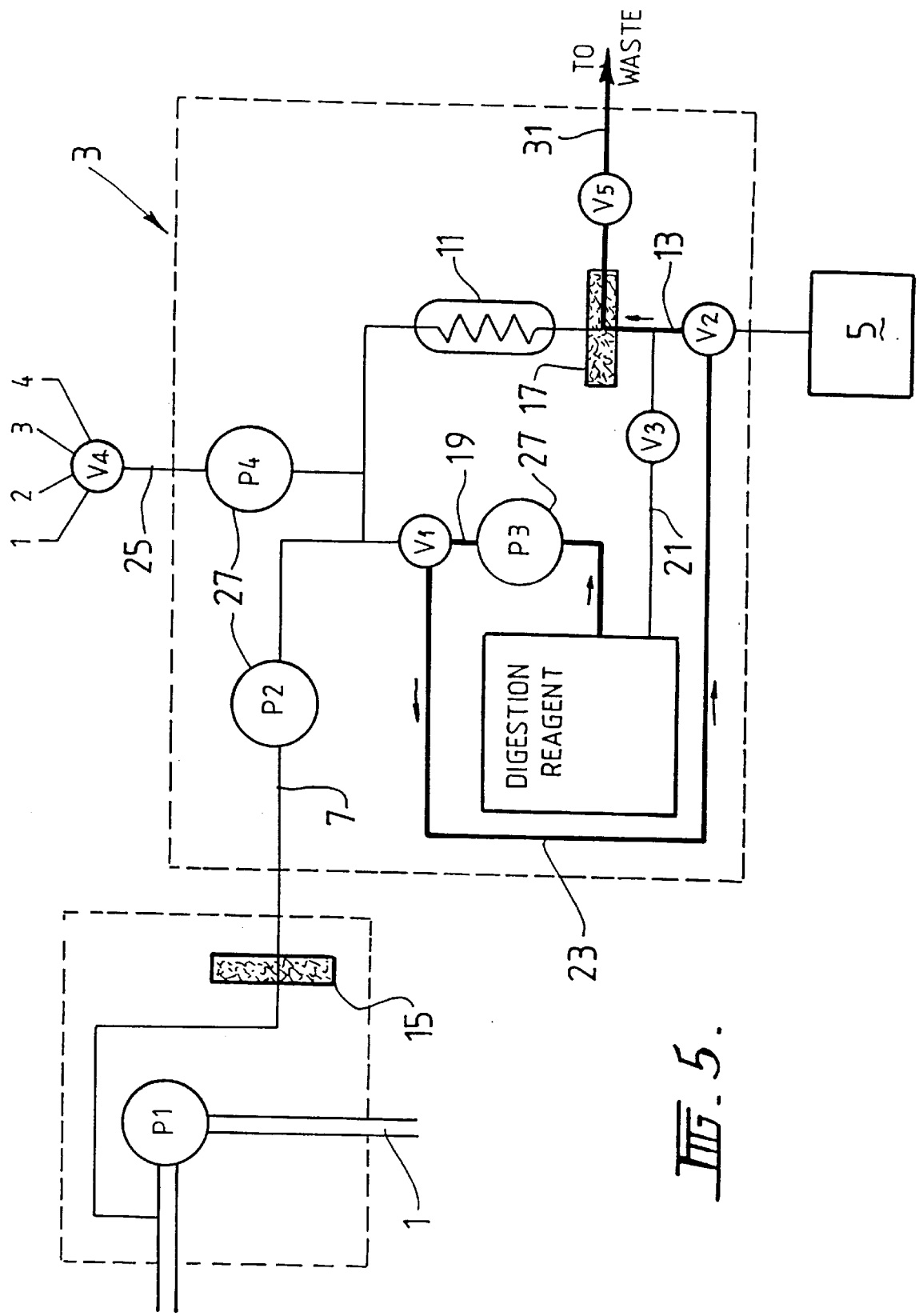
FIG. 5 is a schematic of the flow pattern of a fifth purging step of the first embodiment of the invention.

With reference to FIG. 5, the fifth step of the method comprises purging the filter 17 to discharge any standards reagent retained in the filter 17. In order to carry out the fifth step the valves V3 and V4 are closed, the valves V1, V2 and V5 are opened, and the pump 27 in the digestion reagent line 19 is operated to pump digestion reagent through the reagent line 23 and the filter 17, and thereafter through the waste outlet line 31 to the sump.

At the completion of the fifth step the method steps are repeated after an appropriate period of time has elapsed. In this regard, it can readily be appreciated that the frequency of sampling the effluent will vary depending on a range of factors including, the effluent, the source of the effluent, and environmental or other factors that may influence the concentration of phosphorus in the effluent.

As with the apparatus shown in FIGS. 1 to 5, the apparatus shown in FIGS. 6 to 11 is connected to an effluent line 1 from an industrial plant and is operable to analyze on a real-time basis the concentration of total phosphorus in the effluent.

The basic components of the apparatus shown in FIGS. 6 to 11 are the same as that in FIGS. 1 to 5 and the same reference numerals are used in both sets of drawings to indicate the same components.

One difference between the two embodiments of the apparatus is that the apparatus shown in FIGS. 6 to 11 does not include the reagent supply lines 21, 23 for supplying digestion reagent to the outlet line 13 from the digester 11 that are provided in the apparatus of FIGS. 1 to 5.

Another difference between the two embodiments of the apparatus is in relation to the supply of standards to the inlet line 7 to the digester 11. In the apparatus of FIGS. 6 to 11 the standards, and a blank, are supplied to the inlet line 7 via separate supply lines 61, 63, 65 and valves V1, V2, V3 rather than via a single supply line 25 as in the apparatus of FIGS. 1 to 5.

A further difference is that in the apparatus of FIGS. 6 to 11 the valve V4 in the outlet line 13 from the digester 11 can selectively direct liquid in the outlet line 13 to the waste sump as well as to the analyser/detector 5.

FIGS. 6, 7, 8, and 9 illustrate the flow of digestion reagent with respective flows of effluent (FIG. 6), a first standard (FIG. 7), a blank (FIG. 8), and a second standard (FIG. 9) through the apparatus for the purpose of purging the apparatus of residues that may have been left from previous use of the apparatus prior to subsequent use of the apparatus for analysis and calibration purposes as discussed hereinafter.

Figure 6:
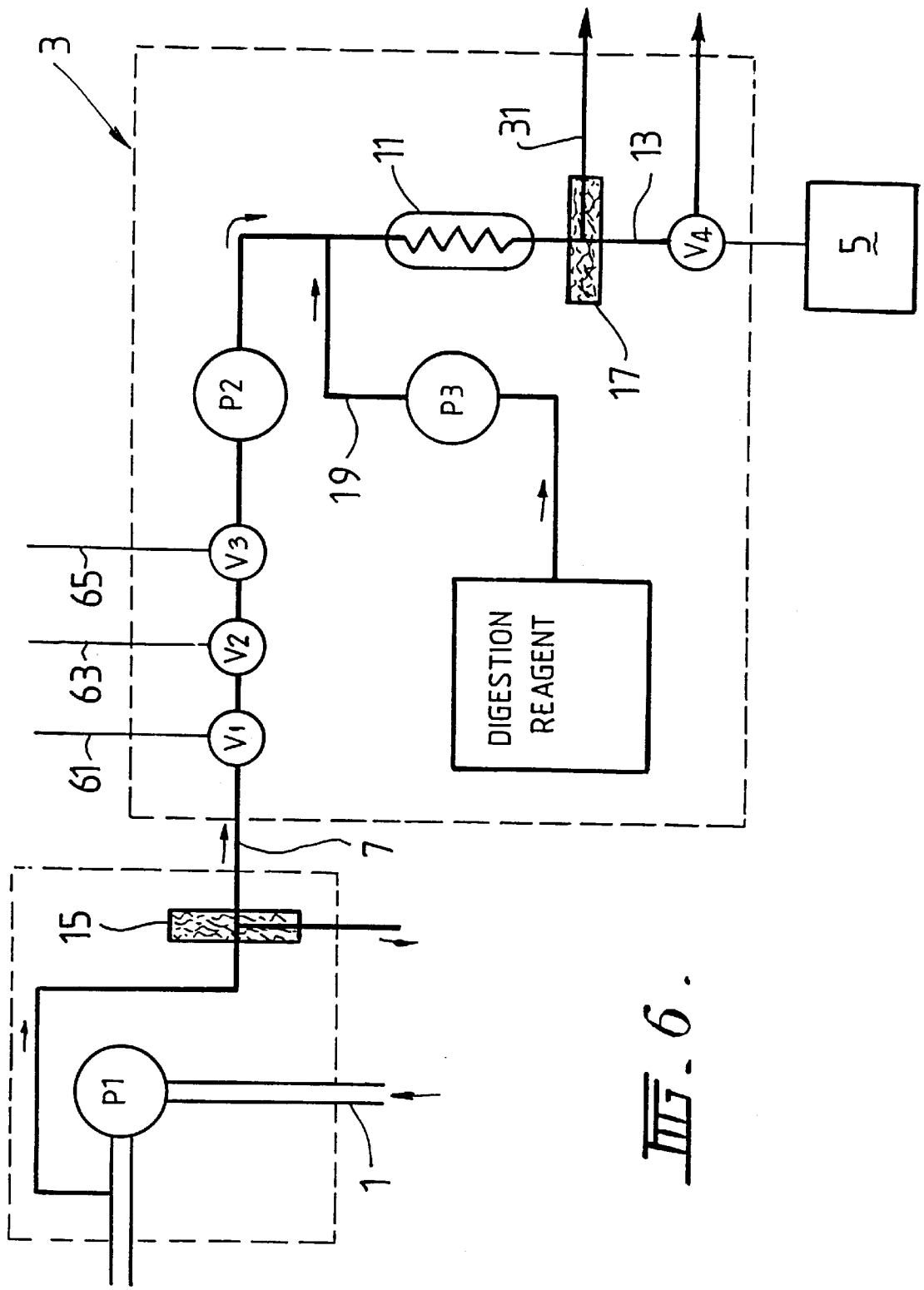
FIG. 6 is a schematic of the flow pattern of a first flushing step of the second embodiment of the invention.

With reference to FIG. 6, in the case of purging with effluent, the valves V1, V2, V3 are closed to prevent flow of the standards and the blank into the inlet line 7, and the valve V4 is closed to prevent flow of liquid to the analyser/detector system 5.

As a consequence, the effluent from the effluent line 1 flows through the inlet line 7 and mixes with digestion reagent which flows via reagent supply line 19 into inlet line 7 and, thereafter, the mixture of effluent and digestion reagent flows through the digester 11. The outlet stream from the digester 11 flows through the filter 17 and thereafter to the waste sump via the filter 17 and via the outlet line 13 and the valve V4.

Figure 7:
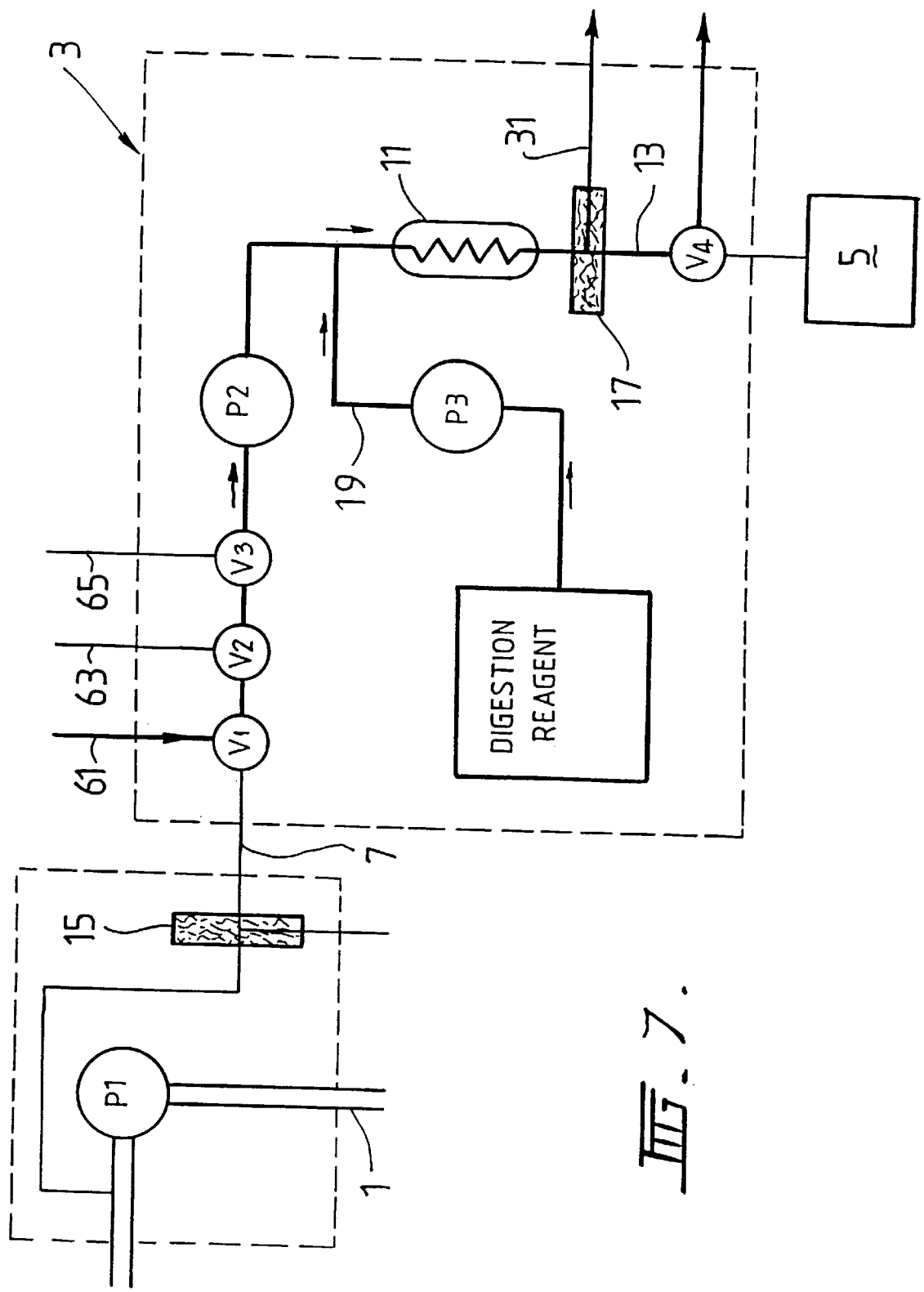
FIG. 7 is a schematic of the flow pattern of a second calibration standard analysis step of the second embodiment of the invention.
Figure 8:
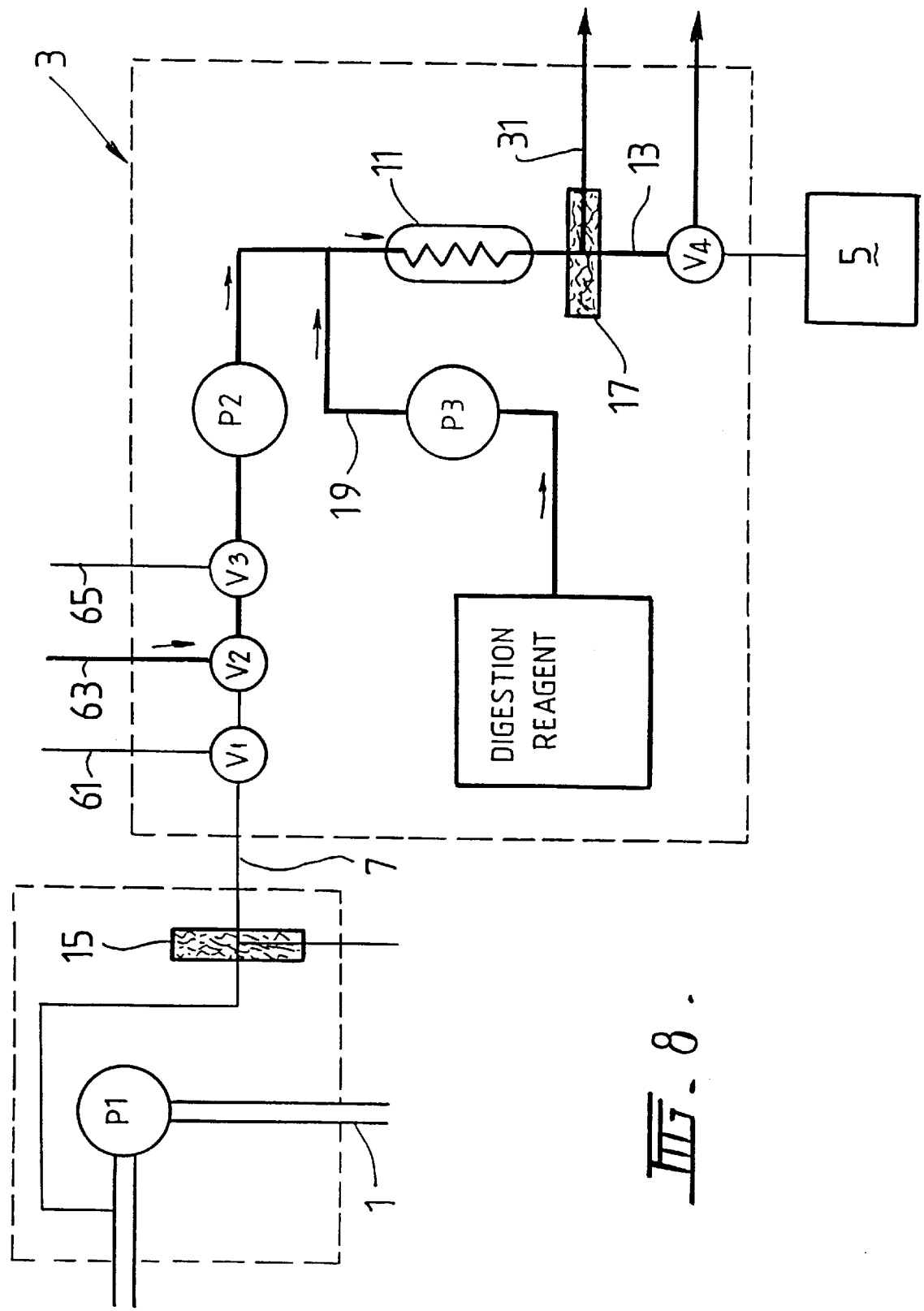
FIG. 8 is a schematic of the flow pattern of a third blank application step of the second embodiment of the invention.
Figure 9:
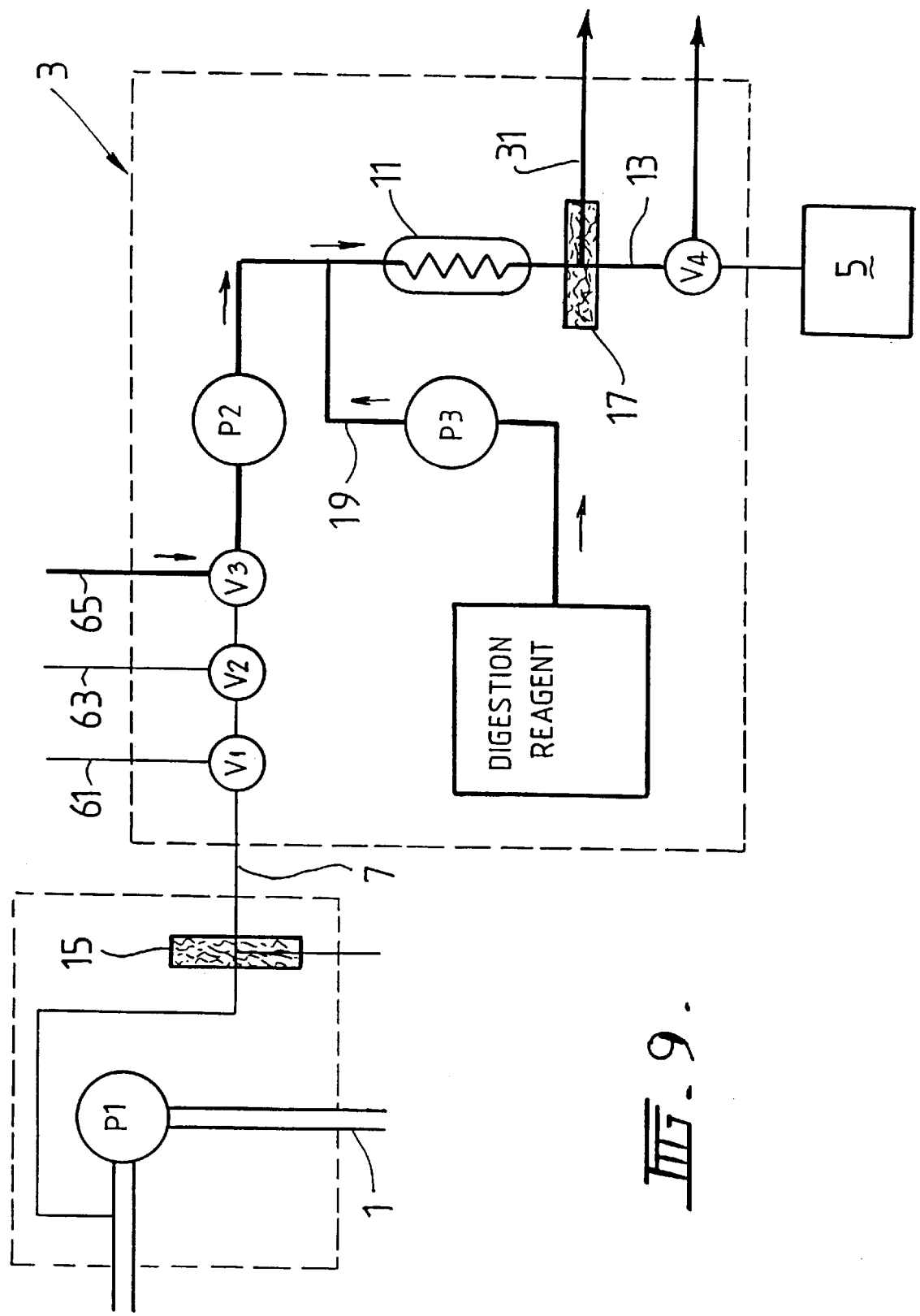
FIG. 9 is a schematic of the flow pattern of a fourth calibration standard analysis step of the second embodiment of the invention.

With reference to FIGS. 7 to 9, the flow paths of the standards and the blank shown in FIGS. 7 to 9 are the same as that in FIG. 6 for the effluent. In each case, the valves V1, V2, V3 are selectively opened/closed to allow one of the standards and the blank rather than effluent to flow via the supply lines 61, 63, 65 into the inlet line 7.

It is preferred that:
(a) the standard referenced "STND 1" in the figures be an orthophosphate or any other suitable compound to calibate the analyser/detector 5;
(b) the blank be de-ionised water; and
(c) the standard referenced "STND 2" in the figures be any suitable compound to check the efficiency of the digester 11.

It is preferred that the STND 1 and the blank be run together, typically at 2 hourly intervals and that the STND 2 be run twice daily. It can readily be appreciated that the frequency of the testing with the standards and the blank may be selected as required.

The purging step of FIGS. 6 to 9 is run for sufficient time to be assured that there are no residues from previous use of the apparatus retained in the digester 11, the filters 15, 17 and the inlet and outlet lines 7, 13.

Figure 10:
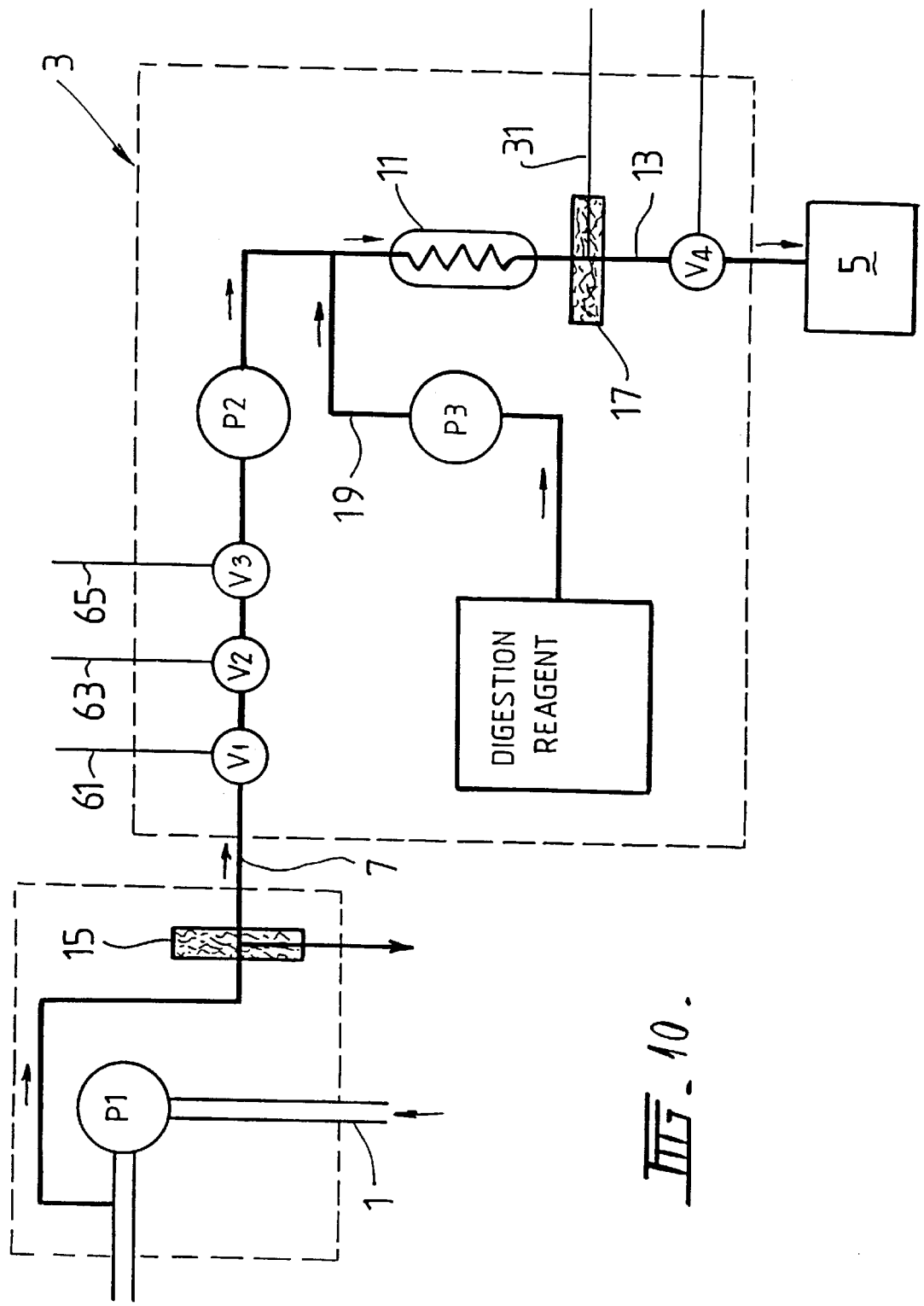
FIG. 10 is a schematic of the flow pattern of a fifth sample analysis step of the second embodiment of the invention.

At this point, in the case of the FIG. 6 arrangement, the apparatus is ready to be operated as illustrated in FIG. 10 to analyse the effluent for total phosphorus.

With reference to FIG. 10, in the analysis step for effluent, the FIG. 6 arrangement is changed by stopping the flows of effluent from the outlet line 13 to the waste sump and opening the valve V4 so that the stream of the digested effluent thereafter flows into the analyser/detector 5. As with the method described in relation to FIGS. 1 to 5, the analysis step is carried out for a sufficient time to allow a minimum volume of the effluent to flow to the analyser/detector 5 to form an analysable sample.

It is noted that in the case of the FIGS. 7, 8, and 9 arrangements, the FIG. 10 arrangement is used to allow testing of the apparatus and the analyser/detector 5 with the standards STND 1 and STND 2 and the blank.

Figure 11:
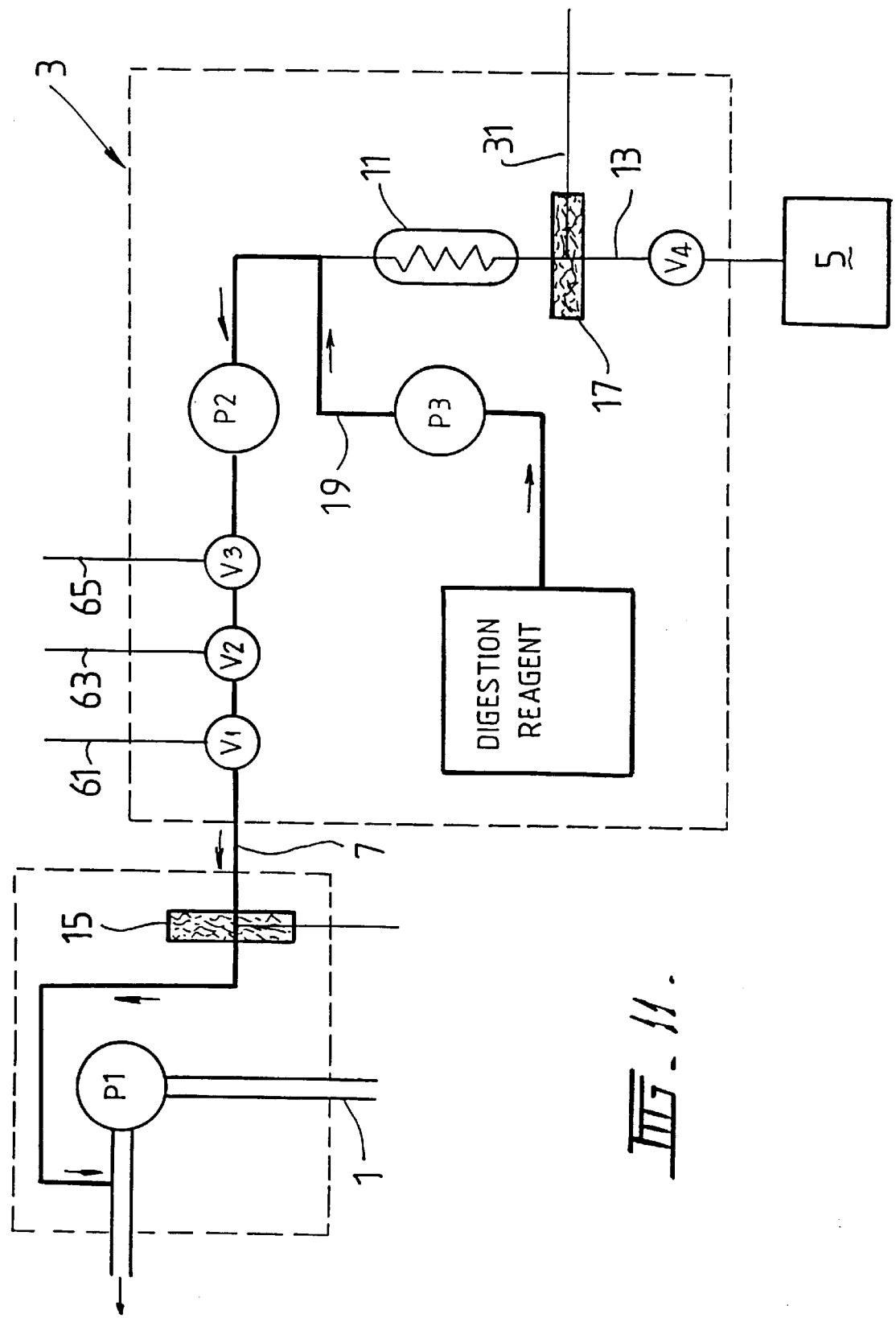
FIG. 11 is a schematic of the flow pattern of a sixth purging step of the second embodiment of the invention.

With reference to FIG. 11, the final step of an effluent analysis cycle comprises purging the inlet line 7 with digestion reagent to dislodge and discharge any solids trapped in the filter 15 and to discharge any biological material in the inlet line 7. It is noted that this step is relatively simplified when compared with the corresponding purging step in the method described in relation to FIGS. 1 to 5 and does not include backflushing through the filter 17 and the digester 11. In this connection, it has been found by the applicant that, generally, the aggressive digester reagent tends to remove any such blockages in filter 17 and retained residues in the digester 11 during the purging step of FIG. 6.

The preferred embodiments of the method and the apparatus of the present invention have a number of advantages over known analysis procedures. By way of example:

(a) the use of filters 15, 17 reduces the risk of the sample preparation section 3 and the analyser/detector 5 being blocked or clogged by solids in the effluent and as a consequence the sample analysis is highly reproducible and controlled in terms of digestion and filtration;
(b) the purging steps in the method ensure that the filters 15, 17 are not blinded by solids and thus the useful life of the filters 15, 17 is relatively long;
(c) the purging steps in the method ensure that the effluent is not retained in the sample preparation section 3 in the periods of time between sampling the effluent and thus reduces the likelihood of phosphorus or other deposits in the lines which could lead to analysis errors;
(d) the method and the apparatus enable rapid digestion (typically 3 to 10 minutes) of the analysable species when compared with the digestion times (typically 30 to 90 minutes) required for known batch procedures;
(e) the method and the apparatus enables the volumes of digestion reagents and effluent samples to be minimised; and (f) in general terms, the apparatus requires minimal maintenance.

Many modifications may be made to the preferred embodiments of the method and the apparatus described above without departing from the spirit and scope of the present invention.

In this regard, whilst the preferred embodiments of the method and the apparatus relate to the analysis of the concentrations of phosphorus, it can readily be appreciated that the present invention is not so limited and extends to any analysable chemical species.

Furthermore, whilst the preferred embodiments of the apparatus include a digester 11 and digestion reagents to place solid forms of phosphorus into the analysable form, it can readily be appreciated that the present invention is not so limited and extends to any suitable means for placing the phosphorus into the analysable form.

Furthermore, whilst the preferred embodiments of the apparatus include 100 and 0.45 micron filters 15, 17 and peristaltic pumps 27, it can readily be appreciated that the present invention is not so limited and extends to any suitable filters and pumps.

Furthermore, whilst the preferred embodiments of the apparatus are constructed for use in the context of on-line analysis of an effluent stream, it can readily be appreciated that the present invention is not so limited and the apparatus may be purpose built for laboratory use.

We claim:

1. A method of analysing a chemical species in a fluid with an analyser system, the analyser system comprising (i) a sample preparation section having a means for placing the chemical species in a sample of the fluid into an analysable form and (ii) an analyser, the method comprising:

(a) purging the sample preparation section with the fluid;

(b) transferring a sample of the fluid into a digester in the sample preparation section via an upstream filtering means and a fluid inlet line and placing the chemical species in the sample into the analysable form by digesting the chemical species with a digestion reagent;

(c) transferring the sample with the chemical species in the analysable form into the analyser and analysing the chemical species in the analyser; and (d) purging the inlet line and the upstream filtering means with the digestion reagent after transferring the sample to the analyser to dislodge any solids retained in the upstream filtering means and to remove any biological material in the fluid inlet line.

2. The method defined in claim 1 comprising purging the sample preparation section after transferring the sample to the analyser to discharge any fluid remaining in the sample preparation section.

3. The method defined in claim 1 comprising purging the sample preparation section after transferring the sample to the analyser to discharge any fluid remaining in the sample preparation section and the filtering means and to dislodge any solids retained in the filtering means.

4. The method defined in claim 1 comprising transferring the sample through a filtering means located downstream of the means for placing the chemical species in the sample into the analysable form in the analyser via an outlet line downstream of the filtering means.

5. The method defined in claim 4 comprising purging the sample preparation section after transferring the sample to the analyser to discharge any fluid remaining in the sample preparation section.

6. The method defined in claim 4 comprising purging the sample preparation section after transferring the sample to the analyser to discharge any fluid remaining in the sample preparation section and the filtering means and to dislodge any solids retained in the filtering means.

7. An apparatus for analysing a chemical species in a fluid, comprising:

(a) an upstream filtering means for the fluid;

(b) a sample preparation section having a digester for placing the chemical species in a sample of the filtered fluid into an analysable form, a means for supplying a digestion reagent to the digester, an inlet line for transferring filtered fluid to the digester, and an outlet line for transferring the sample from the digester;

(c) an analyser for analysing the sample transferred via the outlet line from the digester; and (d) a means for purging the upstream filtering means and the inlet line with the digestion reagent after transferring the sample to the analyser to dislodge any solids retained in the filtering means and to remove any biological material in the sample preparation section.

8. The apparatus defined in claim 7 comprising filtering means downstream of the digester.

9. The apparatus defined in claim 8 comprising a means for purging the sample preparation section and the filtering means after transferring the sample to the analyser to discharge any remaining fluid in the sample preparation section and the filtering means and to dislodge any solids retained in the filtering means.

* * * * *